US00PP22751P2

(12) United States Plant Patent
Smith

(10) Patent No.: US PP22,751 P2
(45) Date of Patent: May 22, 2012

(54) *ASTER* PLANT NAMED 'SYNFROST'

(50) Latin Name: *Aster hybrida*
Varietal Denomination: Synfrost

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 22 days.

(21) Appl. No.: 12/925,473

(22) Filed: Oct. 22, 2010

(51) Int. Cl.
*A01H 5/00* (2006.01)

(52) U.S. Cl. ..... Plt./355

(58) Field of Classification Search ..... Plt./355
See application file for complete search history.

(56) References Cited

U.S. PATENT DOCUMENTS

PP10,645 P * 10/1998 Kristiansen ..... Plt./355
* cited by examiner

*Primary Examiner* — June Hwu
(74) *Attorney, Agent, or Firm* — Joshua L. Price

(57) ABSTRACT

A new *Aster* plant named 'Synfrost' particularly distinguished by the small to medium sized, long lasting, daisy-type inflorescences with white ray floret color, dark yellow-green foliage, upright, freely branched and rounded plant habit, and a natural season flowering of about mid September.

1 Drawing Sheet

Latin name of the genus and species of the plant claimed: *Aster hybrida.*

Varietal denomination: 'Synfrost'.

BACKGROUND OF THE NEW PLANT

The present invention comprises a new *Aster*, botanically known as *Aster hybrida*, and hereinafter referred to by the variety name 'Synfrost'.

'Synfrost' is a product of a planned breeding program. The new cultivar has small to medium sized, long lasting, daisy-type inflorescences with white ray floret color, dark yellow-green foliage, upright, freely branched and rounded plant habit, and a natural season flowering of about mid September.

'Synfrost' originated from a open-pollinated hybridization made in August 2003 in a controlled breeding environment in Salinas, Calif. The female parent was a commercial plant variety designated 'Patricia Viking', U.S. Plant Pat. No. 10,645, with purple-violet ray floret color. 'Patricia Viking' has larger size inflorescences and a more mounded plant habit than 'Synfrost'.

The male parent of 'Synfrost' was an unknown plant. The resultant seed was sown in Alva, Fla. in April 2004.

'Synfrost' was selected as one flowering plant within the progeny of the stated cross in October 2004 in a controlled environment in Alva, Fla.

The first act of asexual reproduction of 'Synfrost' was accomplished when vegetative cuttings were propagated from the initial selection in December 2004 in a controlled environment in Alva, Fla.

BRIEF SUMMARY OF INVENTION

Horticultural examination of plants grown from cuttings of the plant initiated in December, 2004, and continuing thereafter, has demonstrated that the combination of characteristics as herein disclosed for 'Synfrost' are firmly fixed and are retained through successive generations of asexual reproduction.

'Synfrost' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6776). 'Synfrost' has not been made publicly available more than one year prior to the filing of this application.

The following traits have been repeatedly observed and are determined to be basic characteristics of the new variety. The combination of these characteristics distinguishes this *Aster* as a new and distinct variety.

BRIEF DESCRIPTION OF THE PHOTOGRAPHS

The accompanying photographic drawing shows typical flower and foliage characteristics of 'Synfrost' with colors being as true as possible with an illustration of this type.

The photographic drawing shows three flowering potted plants of the new variety growing in one pot and a close-up of the flowers.

DETAILED BOTANICAL DESCRIPTION

The plant descriptions, measurements and aforementioned photographs were taken in Gilroy, Calif. in May 2010 under natural light. These plants used in the photographs and descriptions were about 12 weeks old. Plants were grown in an 8 inch pot with three plants per pot.

Color references are made to The Royal Horticultural Society Colour Chart (R.H.S.) 2001.

TABLE 1

DIFFERENCES BETWEEN THE NEW VARIETY 'SYNFROST' AND A SIMILAR VARIETY: 'MARGRETHE VIKING' (U.S. Plant Pat. No. 10,358)

| | 'Synfrost' | 'Margrethe Viking' (U.S. Plant Pat. No. 10,358) |
|---|---|---|
| Inflorescence lastingness: | 1 week longer | 1 week shorter |
| Quantity of ray florets: | Less | More |

TABLE 1-continued

DIFFERENCES BETWEEN THE NEW VARIETY 'SYNFROST' AND A SIMILAR VARIETY: 'MARGRETHE VIKING' (U.S. Plant Pat. No. 10,358)

| | 'Synfrost' | 'Margrethe Viking' (U.S. Plant Pat. No. 10,358) |
|---|---|---|
| Quantity of disc florets: | More | Less |
| Peduncle length: | Longer | Shorter |

Plant:

*Form, growth and habit*.—Stems upright, freely branching, rounded habit, strong and moderately vigorous growth.

*Plant height*.—About 24 cm.

*Plant height* (*inflorescence included*).—26-28 cm.

*Plant width*.—29-30 cm.

*Garden performance and tolerance to weather*.—Very good.

Roots:

*Number of days to initiate roots*.—10 days at about 22 degrees C.

*Number of days to produce a rooted cutting*.—16-18 days at 22 degrees C.

*Type*.—Fine, fibrous, free branching.

*Color*.—RHS N155B but whiter.

Foliage:

*Arrangement*.—Alternate, simple, sessile.

*Immature, leaf color, upper surface*.—RHS 147A.

*Lower surface*.—RHS 147A but lighter.

*Mature, leaf color, upper surface*.—RHS 147A.

*Lower surface*.—RHS 147A but lighter.

*Length*.—3.4-3.7 cm.

*Width*.—0.7-0.8 cm.

*Shape*.—Narrowly lanceolate to ligulate.

*Base shape*.—Clasping.

*Apex shape*.—Acute.

*Margin*.—Entire.

*Texture, upper surface*.—Mostly glabrous but with a few hairs on the margins.

*Lower surface*.—Mostly glabrous but with a few hairs on the margins.

*Color of veins, upper surface*.—RHS 144A basally becoming indistinct.

*Color of veins, lower surface*.—RHS 144A basally becoming indistinct.

Stem:

*Quantity of main branches per plant*.—3-5, with an abundance of secondary branching.

*Color of stem*.—Closest to RHS 146A.

*Length of stem*.—20-25 cm.

*Diameter*.—0.3 cm.

*Length of internodes*.—1.0-2.0 cm.

*Texture*.—Glabrous.

*Color of peduncle*.—Closest to RHS 137A.

*Length of peduncle*.—5-7 cm.

*Peduncle diameter*.—0.1 cm.

*Texture*.—Glabrous.

Inflorescence:

*Type*.—Compositae type, solitary inflorescences borne terminally above foliage, ray florets arranged acropetally on a capitulum.

*Natural season flowering*.—About mid September in the north.

*Quantity of inflorescences per plant*.—About 50, plus numerous buds.

*Lastingness of individual blooms on the plant*.—About 4 to 4½ weeks.

*Fragrance*.—None.

Bud (just when opening/showing color):

*Color*.—RHS 4C.

*Length*.—0.6-1.0 cm.

*Width*.—0.7-0.9 cm.

*Shape*.—Oblate.

Immature inflorescence:

*Diameter*.—2.5-2.8 cm.

*Color of ray florets, upper surface*.—RHS N155B but whiter.

*Lower surface*.—RHS N155B but whiter.

Mature inflorescence:

*Diameter*.—3.5-4.0 cm.

*Depth*.—0.7 cm.

*Total diameter of 'disc'*.—1.0-1.2 cm.

*Receptacle height*.—0.3 cm.

*Receptacle diameter*.—0.45 cm.

Ray florets:

*Average quantity of florets*.—60-70 in numerous whorls.

*Color of florets, upper surface*.—RHS N155B but whiter.

*Lower surface*.—RHS N155B but whiter.

*Length*.—1.5-1.6 cm.

*Width*.—0.3-0.35 cm.

*Shape*.—Elliptical.

*Apex shape*.—Rounded, retuse and praemorse.

*Margin*.—Entire.

*Texture, upper surface*.—Papillose.

*Lower surface*.—Papillose.

Disc florets:

*Average quantity of florets*.—About 75.

*Color of florets*.—RHS 6C.

*Length*.—0.6 cm.

*Width*.—0.1 cm.

*Shape*.—Tubular, elongated.

*Apex shape*.—Acute, 5 pointed.

Phyllaries:

*Quantity*.—About 20 in several whorls.

*Color, upper surface*.—RHS 147A.

*Lower surface*.—RHS 147A.

*Length*.—0.3-0.6 cm.

*Width*.—0.1-0.15 cm.

*Shape*.—Ligulate.

*Apex shape*.—Acute.

*Based*.—Fused.

*Margins*.—Entire.

*Texture, upper surface*.—Glabrous.

*Lower surface*.—Glabrous.

Reproductive organs:

*Gynoecium*.—Present on both floret types.

*Pistil*.—1.

*Length*.—0.7-0.9 cm.

*Style color*.—RHS 155C.

*Style length*.—0.55 cm.

*Stigma color*.—RHS 6C.

*Stigma shape*.—Bi-parted.

*Ovary color*.—Not observed.

*Androecium*.—Present on only disc florets.

*Stamens*.—1.

*Color of filaments*.—RHS 1D but more translucent looking.

*Length filaments.*—0.3 cm.
*Anther color.*—RHS 3A.
*Anther length.*—0.1 cm.
*Anther shape.*—Ovate to oblong.
*Color of pollen.*—RHS 3D.
*Pollen amount.*—Moderate.
*Fertility/seed set.*—Has not been observed on this hybrid.

Disease/pest resistance: Disease/pest resistance has not been observed on this hybrid.

What is claimed is:

1. A new and distinct variety of *Aster* plant named 'Synfrost' substantially as illustrated and described herein.

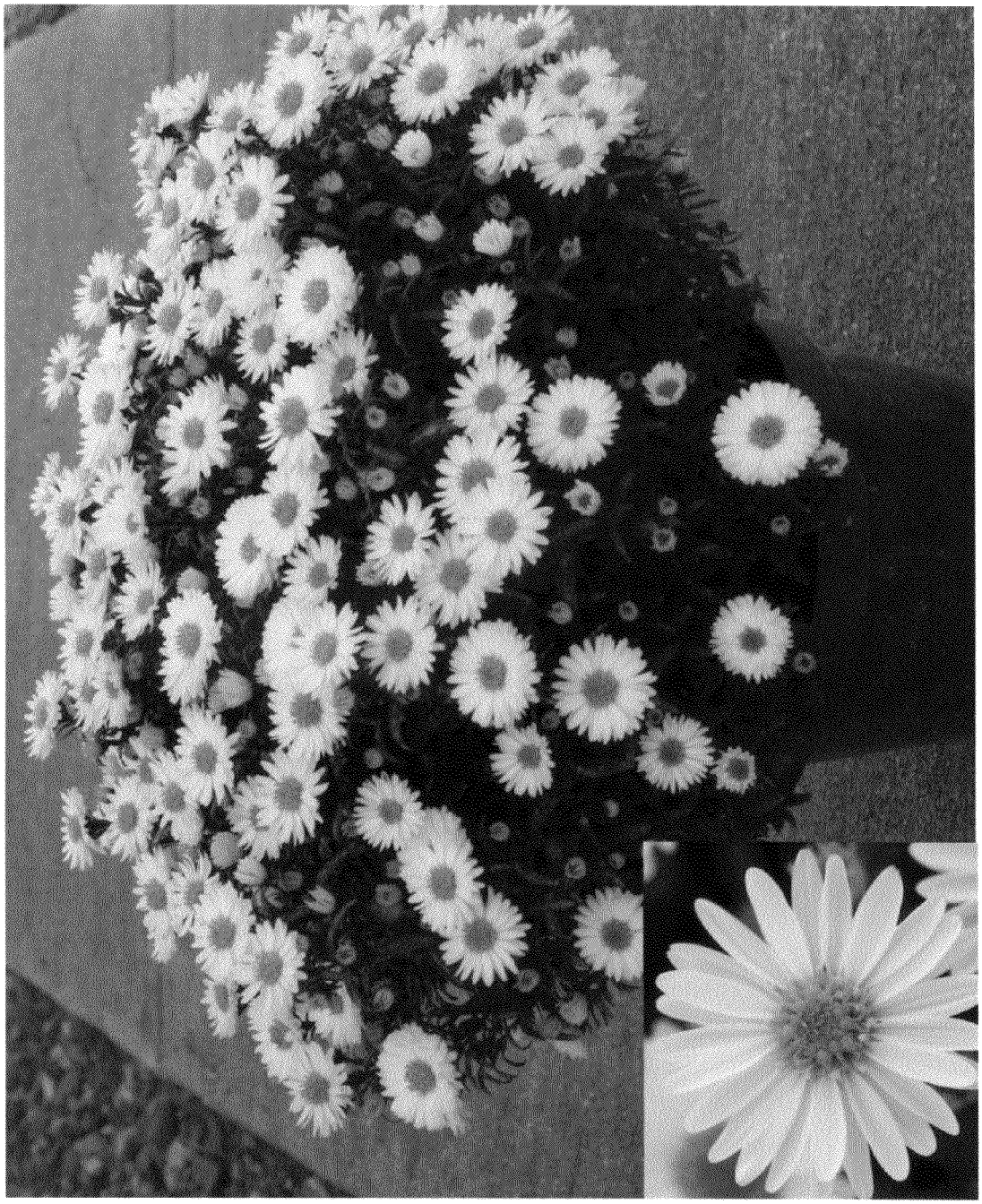

* * * * *